United States Patent [19]
Lin

[11] Patent Number: 5,579,358
[45] Date of Patent: Nov. 26, 1996

[54] COMPENSATION FOR MOVEMENT IN COMPUTED TOMOGRAPHY EQUIPMENT

[75] Inventor: Wen-Tai Lin, Schenectady, N.Y.

[73] Assignee: General Electric Company, Schenectady, N.Y.

[21] Appl. No.: 452,450

[22] Filed: May 26, 1995

[51] Int. Cl.$^6$ ................................. G01N 23/00
[52] U.S. Cl. ................. 378/4; 378/901; 250/363.02; 250/363.04
[58] Field of Search ................. 378/207, 901, 378/4, 62; 250/363.02, 363.04

[56] References Cited

FOREIGN PATENT DOCUMENTS 0177092  7/1988  Japan ................. 250/363.04

OTHER PUBLICATIONS

Wen-Tai Lin, "A Motion Compensation Algorithm for Arbitrary Translation of CT Objects," Feb. 13, 1994, SPIE Medical Imaging 1994, Newport Beach, CA.

*Primary Examiner*—Don Wong
*Attorney, Agent, or Firm*—Donald S. Ingraham

[57] ABSTRACT

A method of real time compensating for patient movement associated with expansion and contraction in computed tomography utilizes the determination of the centroids of successive images, rescaling of each projection data, the alignment of the centroids, and display of the aligned images.

8 Claims, 3 Drawing Sheets

COMPENSATION FOR MOVEMENT IN COMPUTED TOMOGRAPHY EQUIPMENT

BACKGROUND OF INVENTION

This invention relates to compensation for patient or other movement in computed tomography equipment and operation, and in particular to an improved method for mitigating blurring and streaking in computed tomography (hereinafter "CT") caused by movement of the object being imaged or the CT equipment during imaging.

Blurring and streaking caused by movement during imaging is a well-known, but difficult to solve problem in CT equipment. Such movements, in the case of medical CT imaging may be, for example, patient movement. The principle present solution to the problem is attempting to avoid movement during imaging. This includes in the case of medical CT imaging breathholding by the patient to briefly avoid the patient's periodic motions, such as respiratory activities. However, such techniques are generally not particularly useful and applicable to critically ill patients, infants, and involuntary organ motions. Various attempts to minimize the problem include efforts to design faster scanning equipment not as susceptible to movement problems, but which is necessarily more complex and expensive and which does not enhance resolution; the use of volummetric CT based on cone-beam and planar detector arrays; attempts to measure the motion to compensate for it; and post-processing the image data obtained with algorithmic approaches. These techniques have not proven able to handle all possible patient motions such that the various approaches to solving the problem of patient motions have not proven entirely satisfactory. In addition, there are other odd categories of motion perturbations such as the equipment platform or mechanical jittering when, for example, a heavy truck passes the building or room in which the equipment is positioned, cardiac and respiratory motions, and a shift of X-ray focal spot. It becomes extremely diffcult to provide sensors which can measure such movements as a basis for compensation of the movements. As a result, it is desirable that a compensation method not be based on the addition of motion sensors or detectors and the measurements or signals provided by motion sensors or detectors.

In addition, it is highly desirable that any compensation provided for patient movement be applicable not only to the design and construction of new equipment, but also to be applicable and suitable for readily retrofitting or incorporating into existing CT equipment because of the considerable number of existing CT equipments which exhibits blurring, streaking, and poor image resolution as a result of patient motion (i.e, expansion and contraction). Moreover, it is highly desirable that motion compensation equipment and methods be applicable to both parallel and fan beam scanning systems, and also to cone scanners.

It is also desirable that the method for compensating for movement in CT equipment be relatively uncomplex and relatively inexpensive to facilitate its ready incorporation into various types of CT equipment, including existing equipment. Although there are a wide variety of motion functions, the type of problem dealt with by this invention is limited to (1) motions occuring in the same plane defined by the position of the X-ray beam in two dimension CT and (2) motion occuring within the same cone defined by the X-ray source and the detector array. Correction for translational motion only is discussed in W. T. Lin "A Motion Compensation Algorithm for Arbitrary translation of CT Objects", *SPIE Medical Imaging,* 1994, Feb. 13–14, 1994, Newport Beach, Calif., pp. 743–754.

OBJECTS AND SUMMARY OF INVENTION

It is an object of the present invention to provide a method of motion compensation for CT scanning capable of compensating for patient movement associated with expansion and contraction.

It is another object of the present invention to provide a method of motion compensation in CT scanning which does not require obtaining, and/or explicit knowledge about, the transitional functions or actual measurement of motion.

It is still another object of the present invention to provide a method of motion compensation in CT scanning which is applicable to both parallel and fan beam scanners.

It is a further object of the present invention to provide a method of motion compensation in CT scanning which is based on an inherent property of the scanned object rather than being sensor-based and which facilitates retrofitting into existing CT equipment.

In accordance with one form of the invention, a method of compensating for patient motion associated with expansion and contraction in computed tomography scanning involves determining the centroids of the object being scanned by successive image scans, aligning the centroids of successive image scans and displaying the aligned centroid image scans. An iterative technique includes the reprojecting of an initial image scan to provide an initial projection, comparing the centroid displacement between subsequent image scans and the initial projection, and realigning the projection data in response to the centroid displacement to improve the reconstructed image; and iteratively continuing the rescaling and realigning until there is no longer significant changes in the reconstructed image. The scaling factor is based on the magnitude of the entropy difference between successive image scans and the pilot image scan. The method is applicable to parallel beam, thin fan beam, and cone beam scanning, and is suitable for retrofitting into existing equipment.

BRIEF DESCRIPTION OF INVENTION

Figure 1:
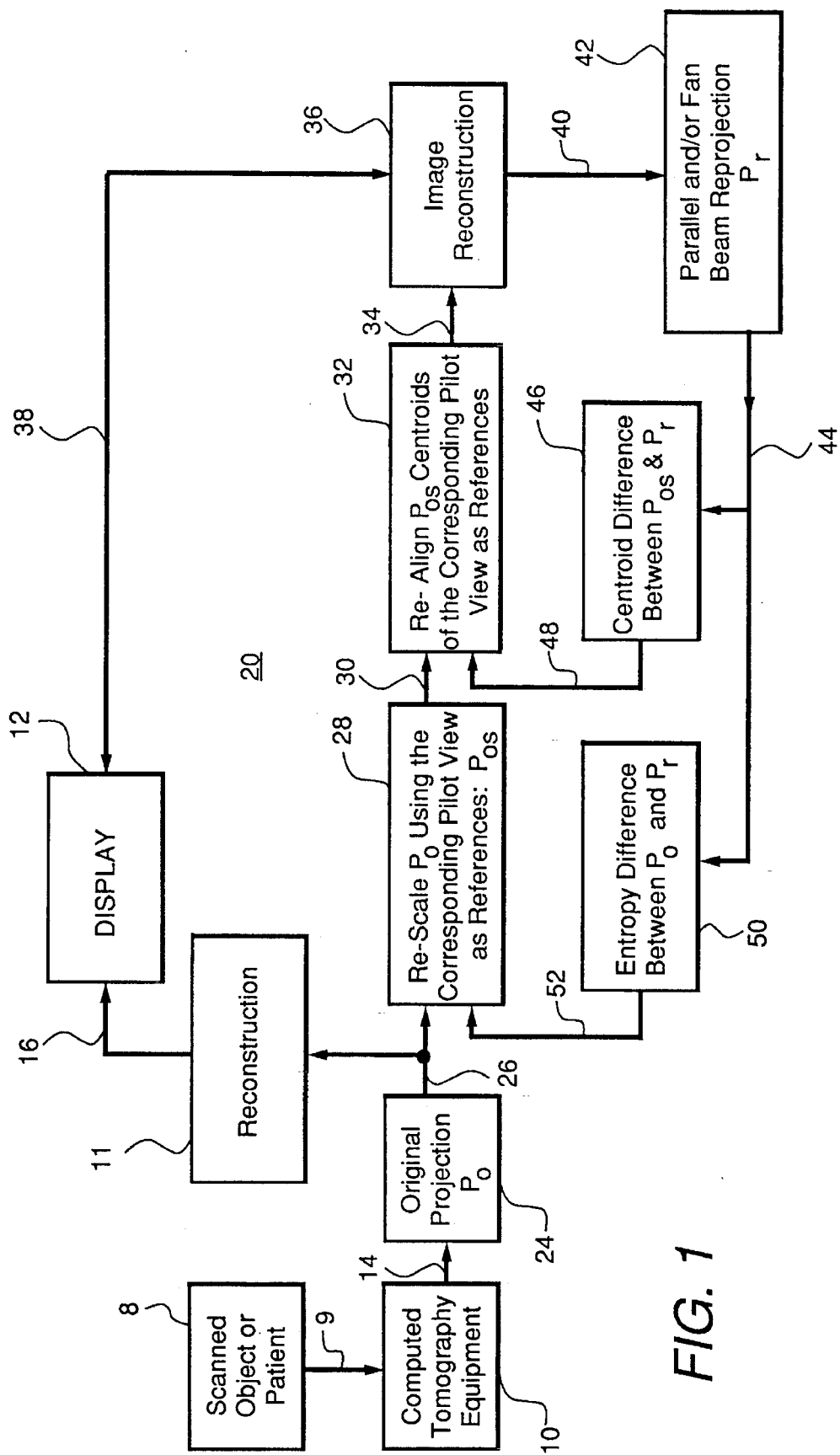
FIG. 1 is a block diagram showing the present invention.

Referring first to FIG. 1, computed tomography (CT) equipment 10 is utilized to scan the scanned object, or patient 8 in the case of medical CT, to provide a scanned projection data signal 26 in a manner well known in the art. Projection data signal 26 is generated in response to gantry scan 9 and a reconstruction technique 11 is applied to generate a display image signal 16 to display circuitry 12.

In accordance with the present invention, scanned projection data 26 is passed through motion compensation means 20 for generation of motion compensated display signal 38. An initial reference projection $P_r$ in the form of signal 44 is obtained by reprojecting the image reconstructed from $P_o$ (without motion compensation). Initial projection $P_o$ 26 is rescaled 28 based on the relative spread between $P_o$ and $P_r$ obtained from the previous iterations, that is generally based on the entropy difference between $P_o$ and $P_r$.

Rescaled projection $P_{os}$ 30 is aligned using the centroids of projection $P_r$ as references. Image reconstruction 36 is continued to generate a new image, followed by reprojection, to produce a new reference 44 $P_r$ until there is no longer any significant change in the motion compensation reconstructed image 38 which is provided to display 12 to display the motion compensated image of scanned object or patient 8.

The iterative rescaling and realignments are controlled by reconstructed image 36, 40 which is fed back through beam reprojection $P_r$ 42 which may accomodate parallel and/or fan beam equipment as described in more detail below. Reprojected view signal 44 is provided to estimate centroid difference means 46 which estimates the centroid difference between rescaled projection signal $P_{os}$ 30 and reprojected view signal $P_r$ 44.

Reprojected view signal $P_r$ 44 is also provided as input 50 to estimate entropy difference between $P_o$ 26 and $P_r$ 44 to provide entrophy difference 52.

The centroid realignment of the successive images provides an enhanced motion compensated image 38 which mimimizes image blurring or streaking, improving the resolution of the compensated image displayed on display 12.

It is to be noted that the present invention does not require a motion sensor or the generation of any new or different signals by CT equipment 10. In addition, there is no requirement for the determination or use of a prior knowledge about the object or patient's motion, nor an explicit knowledge about the translational or scaling functions. Instead, the present invention exploits inherent properties of the scanned object and requires as an input only the provision of scanned patient or object image signal 16 which otherwise would be provided directly to display 12. However, instead of the display showing images which are reconstructed from misaligned projections which would result in blurring and streaking of the image due to the patient motion, successive projections are aligned and realigned to eliminate the effects of motion and to improve resolution. Improved resolution, of course, enables more accurate and better diagnoses of problems or disease in the scanned object or patient.

In the case of parallel beam scanning, a single iteration is sufficient to provide the compensated image, thus providing real time or substatially instantaneous motion compensation. In the case of fan beam scanning as many as 10 or more iterations of motion compensation means 20 may be required for compensation. While this is accomplished very quickly, with each iteration requiring in the order of only one millisecond, it does not constitute real time compensation because of the slight delay involved in the iterations.

To obtain the most accurate centroid coverage and measurements the motion compensated for should be in-plane for two dimension CT imaging. In the case of 3-D CT imaging the entire object should be covered by the cone beam. It is to be noted that the entropy of a projection snapshot p(x) can be approximated as:

$$E = \frac{\int p^2(x)dx}{\int p(x)dx}$$

such that P(x) can be rescaled by entropy being increased (or reduced) by inserting (or deleting) zeros in the frequency domain of P(x).

Figure 2:
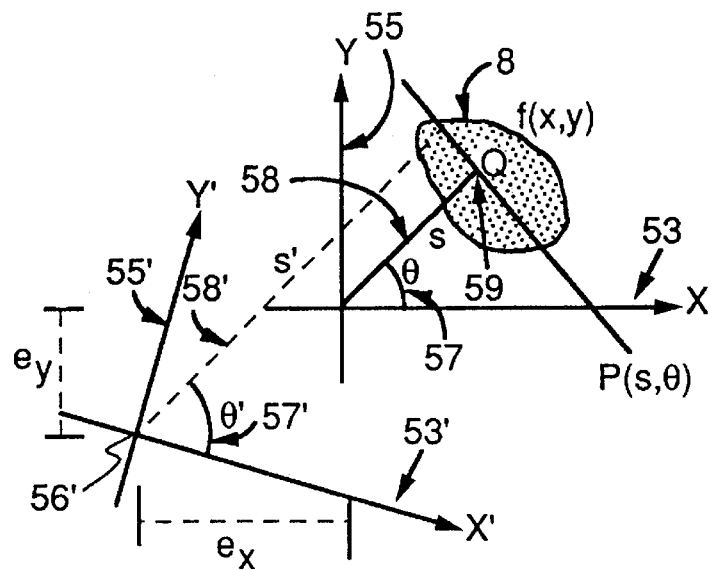
FIGS. 2 and 3 are diagrams useful in explaining the present invention.
Figure 3:
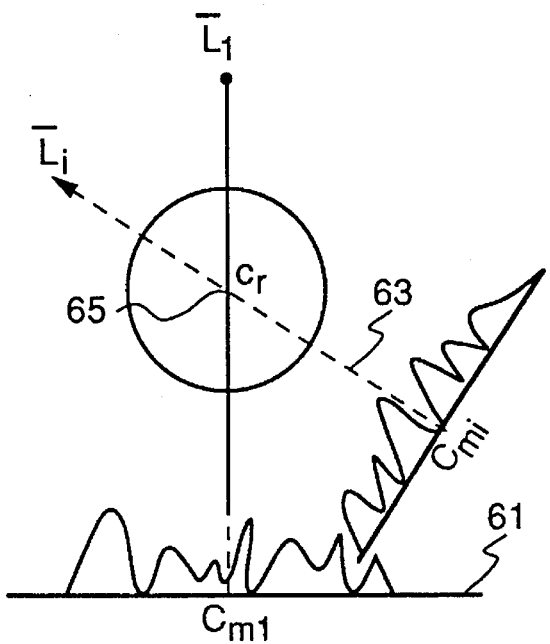
Figure 4:
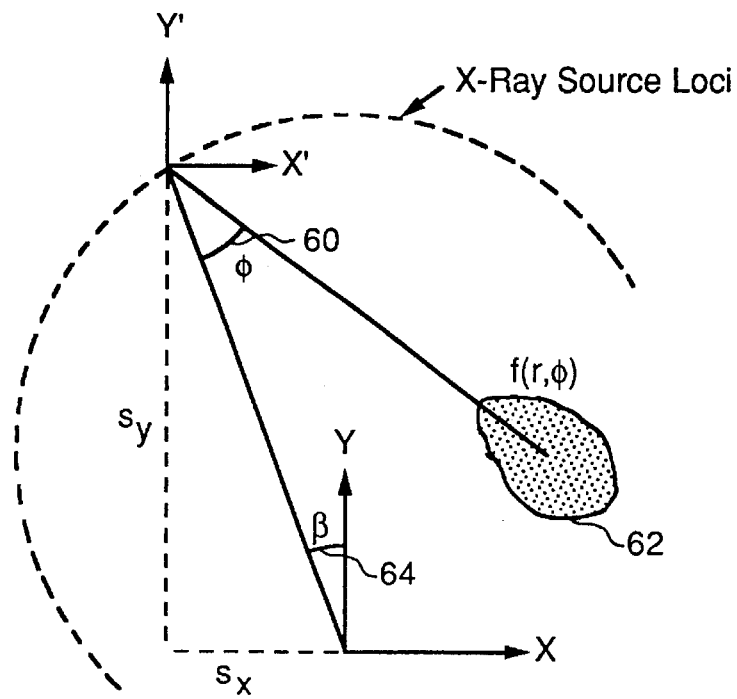
FIG. 4 is a diagram useful in explaining projections in a two coordinate system in accordance with the present invention.

FIGS. 2–4 are helpful in understanding the theory and operation of FIG. 1 motion compensation. Referring first to FIG. 2, which illustates the generic case for both fan beam and parallel projectors, which projections require however slightly different implementation as discussed below in connection with FIGS. 3 and 4, respectively.

The relationship between axes X-Y and X'-Y' coordinates is illustrated in FIG. 2. Referring to FIG. 2, object 8 is assumed to be stationary with X-Y coordinates 53 and 55 respectively, while linearly distorted from the view point of X'-Y' coordinates 53' and 55', respectively. P(s,θ) is a projection ray passing a point Q 59 in the object, with $\overline{QO}$ perpendicular to the ray. The angle θ 57 is the angle between axis X 53 and $\overline{QO}$. The angle θ' 57' is the angle between displaced axis 53' and the angle from origin 56' to a line 58' parallel to line 58 extending from origin 56 to Q 59. The resulting relationships discussed above and below is linear in space. A linear transformation exists between the stationary coordinate system X-Y (53–55) and the time varying coordinate system X'-Y' (53'-55').

To understand the relationship of FIG. 2, let f(x(O), y(O)) be the intensity function of a two dimensional object 51 observed at t=0, positioned relative to axis X 53 and axis Y 55 as indicated. The motion is a time-varying, linear geometric distortion, such that at time t the "pixelated" object f(x(t)y(t)) is related to f(x(O), y(O)) by:

$$\begin{bmatrix} x(t) \\ y(t) \end{bmatrix} = \begin{bmatrix} a(t) & b(t) \\ c(t) & d(t) \end{bmatrix} \begin{bmatrix} x(0) - s_x(t) \\ y(0) - s_y(t) \end{bmatrix} + \begin{bmatrix} e_x(t) \\ e_y(t) \end{bmatrix} =$$

$$\begin{bmatrix} a(t) & b(t) \\ c(t) & d(t) \end{bmatrix} \begin{bmatrix} x(0) \\ y(0) \end{bmatrix} + \begin{bmatrix} e_x(t) \\ e_y(t) \end{bmatrix}$$

where $(s_x(t),s_y(t))$ is the scaling or rotation center at t and $(e_x(t), e_y(t))$ is the relative translation vector between the moving and stationary coordinates. At any viewing time there always exists a homogenous transformation that maps the moved or linearly distorted object back to when it was observed at t=0. Consequently there are 6 model parameters, assuming $(s_x(t),s_y(t))=(O,O)$, to be estimated for each snapshot. Dropping the time index provides the simplified expression:

$$\begin{bmatrix} x' \\ y' \end{bmatrix} = \begin{bmatrix} a & b \\ c & d \end{bmatrix} \begin{bmatrix} x \\ y \end{bmatrix} + \begin{bmatrix} e_x \\ e_y \end{bmatrix}.$$

Let p(s,θ) be a ray integal defined as $$p(s,\theta) = \iint f(x, y)\delta(x\cos\theta + y\sin\theta - s)dxdy.$$

Since the linear distortion in f(x,y) can be viewed as the same object being observed in a new coordinate system, x'-y'. The new line integral can be expressed as:

$$p'(s',\theta') = \iint f(x',y')\delta(x'\cos\theta' + y'\sin\theta' - s') dx'dy' =$$

$$\iint \frac{f(x,y)}{|ad-bc|} \delta((ax + by + e_x)\cos\theta' + (cx + dy + e_y)\sin\theta' - s')dxdy.$$

The delta function in both of the above relationships describe the same line function in the two coordinate systems shown in FIG. 2. Substituting the variables, provides the following:

$$(ax+by+e_x)\cos\theta'+(cx+dy+e_y)\sin\theta'-s'=k(x\cos\theta+y\sin\theta-s)$$

where k is a constant for the ray. The relationship between (s,θ) and (s',θ') is thus given as follows:

$$k = [(a\cos\theta'+c\sin\theta')^2+(b\cos\theta'+d\sin\theta')^2]^{1/2}.$$

$$\theta = \tan^{-1} \frac{b \cos \theta' + d \sin \theta'}{a \cos \theta' + c \sin \theta'},$$

and $$s = (s' - e_x \cos\theta' - e_y \sin\theta')/k.$$

From the above, the mapping for object translation, rotation, and scaling can be derived:

1. For translation only: $a=d=1$ and $b=c=0$, therefore $\theta=\theta'$ and $s=s'-e_x\cos\theta'-e_y\cos\theta'$
2. For rotation only: let $a=d=\cos\alpha$ and $b=c=\sin\alpha$, then $\theta=\theta'=\alpha$, and $s=s'$.
3. For scaling only: let $b=c=0$, then $\theta=\tan^{-1}(d \sin\theta'/(a\cos\theta'))$ and $s=s'/(a^2\cos^2\theta'+d^2\sin^2\theta')^{1/2}$ Note that the above relationship is based on a line integral such that it does not relate to any particular types of CT scanners. Therefore, it is applicable to both fan beam and parallel projections. It is to be noted that the types of motion involved are translation and scaling.

The following assists in showing and understanding that the object 8 translation can be detected using centroid theory as set forth in the aforementioned Lin SPIE Medical Imaging 1994 paper. The centroid can be accurately derived from the parallel projection data, and used as reference points for aligning the projection data acquired at different snapshots. Since the centroid of each snapshot is independently calculated and lined up to a stationary reference, there is no constraint on the object's inter-snapshot translation. In other words, the translation can be arbitrary in time.

For parallel-beam CT applications, the centroid of a rigid object is invariant to the gantry angles, but sensitive to the object's translation incurred during the scanning cycle. Given a 2D object $f(x,y)$, the x and y components of the centroid is:

$$C_x = \frac{\iint x f(x,y) \, dxdy}{\iint f(x,y) \, dxdy} = \frac{\int x P_y(x) \, dx}{\int P_y(x) \, dx},$$

$$C_y = \frac{\iint y f(x,y) \, dxdy}{\iint f(x,y) \, dxdy} = \frac{\int y P_x(y) \, dy}{\int P_x(y) \, dy}.$$

where $P_y(x)$ and $P_x(Y)$ are projection functions of $f(x,y)$ along the y and x directions, respectively. If the object is stationary, only two projection snapshots are needed to calculate $(C_x, C_y)$ and the centroid would maintain stationary throughout the entire scan. However, with motion and a time-varying centroid, $(C_{x'}, C_{y'})$, the relationship between ($C_{x'}, C_{y'}$) and ($C_x, C_y$) is as follows:

$$\begin{bmatrix} C_{x'} \\ C_{y'} \end{bmatrix} = \begin{bmatrix} a & b \\ c & d \end{bmatrix} \begin{bmatrix} C_x \\ C_y \end{bmatrix} + \begin{bmatrix} e_x \\ e_y \end{bmatrix}.$$

Two unknowns can be solved from the above relationship when the rest of the motion parameters are known. If the object's translational motion is the only concern and no other type of motion is involved, then $a=d=1$ and $b=c=0$, and the displacement of object 8 can be directly calculated as:

$$e_x = C_{x'} - C_x; \quad e_y = C_{y'} - C_y.$$

To avoid computing $C_{x'}$ and $C_{y'}$ for each projection snapshot the following simplified procedure shown diagramatically in FIG. 3 may be utilized.

Referring to FIG. 3 and FIG. 1:

1. Use the first projection snapshot of Po 26 as a reference, and compute its center-of-mass, $C_{m1}$, along the axis 61 of the detector array of CT equipment 10.
2. Determine the $L_1$ parallel with the X-ray that passes through $C_{m1}$.
3. For the next projection snapshot, compute its center-of-mass, $C_{m2}$, and compute the line in parallel with the X-ray, $L_2$; shift $L_2$ parallelly such that it intersects with $L_1$ near the center of $C_r$ 65 of the scanner.
4. For any subsequent snapshot i, compute its center-of-mass $C_{mi}$ and compute the parallel line $L_i$; and shift $L_i$ such that $L_i$ passes through $C_r$ 63.

As a result, whenever $L_i$ moves, its associated projection data also moves and is positioned accordingly for back projection. Referring next to FIG. 4, for divergent rays acquired from a fan beam scanner of CT equipment 10, a reference point for each projection angle φ shown as 60 can be established. An obvious difference between the parallel and fan beam formulation is that the latter fits naturally in a polar coordinate system, while the former can be better described in a rectangular coordinate system. Accordingly, to take advantage of the fan beam geometry, a polar coordinate system may be utilized with its origin coincides with the focal spot of the X-ray source. A measurable quantity, fan beam centroid guides the projection alignment. Given a 2D object $f(r,\phi)$ shown as 62, the radial and angular components of the fan beam centroid at view angle β shown as 64 are defined as $$C_r = \frac{\iint r f(r,\phi) \, drd\phi}{\iint f(r,\phi) \, drd\phi} = \frac{S_p}{S_f},$$

$$C_\phi = \frac{\iint \phi f(r,\phi) \, drd\phi}{\iint f(r,\phi) \, drd\phi} = \frac{S_\phi}{S_f}$$

where $S_p = \iint f(r,\phi) \, r \, drd\phi = \iint f(x,y) \, dxdy \approx \Sigma p_p(n\Delta s)$ = sum of parallel beams.

$S_f = \iint f(r,\phi) \, drd\phi = \int p_f(\phi) \, d\phi \approx \Sigma p_f(n\Delta\phi)$ = sum of fan beams.

$S_{100} = \iint \phi f(r,\phi) \, drd\phi \approx \Delta\phi \Sigma n \, p_f(n\Delta\phi)$, with $p_p$ and $p_f$ designated as parallel and fan beam projections, respectively. Since $p_f$ is dependent on the source location, both $S_f$ and $S_\phi$ (and, likewise, $C_r$ and $C_\phi$) are view dependent. As an example, $C_r$ may be expressed as $$C_r = \frac{\iint f(x',y') \, dx'dy'}{\iint \frac{f(x',y') \, dx'dy'}{(x'^2+y'^2)^{1/2}}} = \frac{\iint f(x,y) \, dx \, dy}{\iint \frac{f(x,y) \, dxdy}{[(x-x_s)^2+(y-y_s)^2]^{1/2}}}$$

where the numerator is the sum of a parallel projection snapshot (which is a constant for all CT gantry angles), while the denominator is a function of the source location $(x_s, y_s)$. The result is that the fan beam centroid is no longer invariant to CT gantry rotation.

Let $\{(C_{rm}(\beta)), C_{\phi m}(\beta)) \mid \beta \in [0, 2\pi]\}$ be a set of fan beam centroids derived from a time-varying object with projections 26 acquired at all gantry angles. A set of reference centroids, $\{C_{rs}(\beta), C_{\phi s}(\beta)) \mid \beta \in [0, 2\pi]\}$ is derived such that the centroid diffrence $\{C_{rm}(\beta)-C_{rs}(\beta), C_{\beta m}(\beta)-C_{\phi s}(\beta))\}$ 48 corresponds to the relative translation at angle β of scanned object 8. Starting with a pilot or original projection set, initially obtained by reprojecting the uncompensated image, a consistent representation of a stationary object similar to the original one may be obtained. Hence, the reprojection set is motion free. As the number of interations increases, the reconstructed image provided on display 12 will be further improved through centroid alignment.

Figure 5:
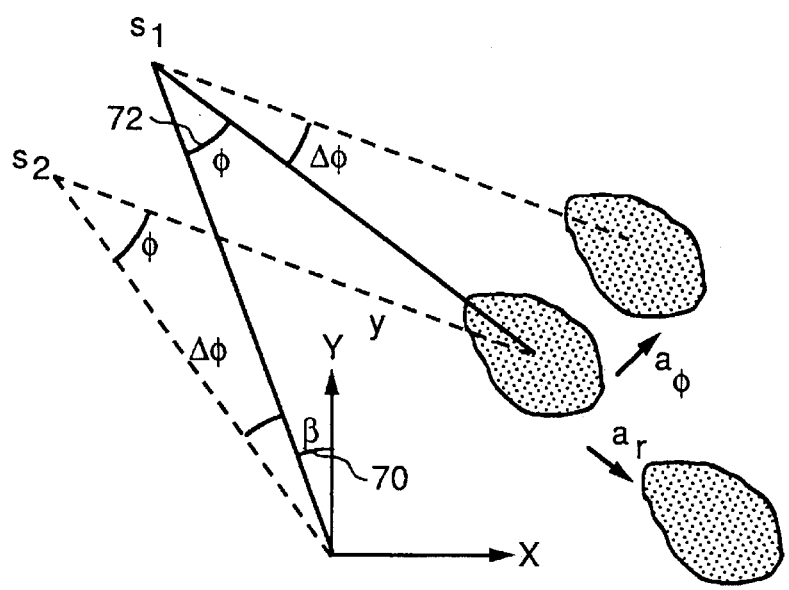
FIG. 5 is a diagram useful in explaining object translation.

FIG. 5 shows that the translation of an object in the radial direction of the fan beam causes an equivalent scaling effect in the projection data, while translating in the azimuthal direction introduces an equivalent object rotation, in addition to a misalignment in the detector dimension. If $P_o(\beta,\phi)$ is a projection ray of a moving object, f,62 with $\beta$ 70 specifying the CT gantry angle and $\phi$ the ray angle, the following describes the iterative algorithm for evolving a set of reference points, $\{(C_{rs}(\beta), C_{\phi s}(\beta))\}$, such that, when used for projection alignment, these points converge to a set of fan beam centroids equivalent to a stationary form of the same object, and the motion-perturbed projections are thereby correctly realigned as described in the following:

1. Reconstruct an image, $f_s$, from the original projection set $P_o = \{p_m(\beta,\phi)\}$ with $\beta$ shown as 70 and $\phi$ as 72 in FIG. 5.
2. Obtain a pilot projection set $P_s = \{p_s(\beta,\phi)\}$, by reprojecting the image $f_s$, with fan beam geometry.
3. Rescale $P_o$ to $P_m$ such that for each $\beta$, $P_m(\beta,\phi)$ and $P_s(\beta,\phi)$ have the same entropy.
4. Obtain a parallel projection set $P_p = \{P_p(\beta,s)\}$, by reprojecting $f_s$ with parallel-beam geometry.
5. Compute $(C_{rs}(\beta), C_{\phi s}(\beta))$ as follows:

$$C_{rs}(\beta) = \frac{\sum_n p_p(\beta, n\Delta s)\Delta s}{\sum_n p_s(\beta, n\Delta\phi)} \; ; \; C_{\phi s}(\beta) = \frac{\Delta\phi \sum_n n\, p_s(\beta, n\Delta\phi)}{\sum_n p_s(\beta, n\Delta\phi)}.$$

6. Similarly, compute $(C_{rm}(\beta), C_{\phi m}(\beta))$ as follows:

$$C_{rm}(\beta) = \frac{\sum_n p_p(\beta, n\Delta s)\,\Delta s}{\sum_n p_m(\beta, n\Delta\phi)\Delta\phi} \; ; \; C_\phi m(\beta) = \frac{\Delta\phi \sum_n n p_m(\beta, n\Delta\phi)}{\sum_n p_m(\beta, n\Delta\phi)}.$$

7. Compute the centroid difference measured at projection angle 70 $\beta$; that is, $$\Delta C_r(\beta) = C_{rm}(\beta) - C_{rm}(\beta); \text{ and } \Delta C_\phi(\beta) = C_{\phi m}(\beta) - C_{\phi s}(\beta).$$

8. In the filtered backprojection process, adjust the X-ray source position such that the distance from the source to the ISO center is increased by $\Delta C_r(\beta)$.
9. Likewise, to adjust for $\Delta C_r(\beta)$, reign the projection data in detector dimension according to the shifted ray angle $\Delta C_\phi(\beta)$, and meanwhile, readjust the projection angle such that $\beta' = \beta + \Delta C_\phi(\beta)$. $\beta$ is modified to undo the equivalent rotation effect due to the translation in azimuthal direction.
10. Repeat step 4 to 9 for all gantry angles and then reconstruct a new image, $f_{s'}$, from the realigned protections $P_{m'} = \{p_m(\beta, \phi + \Delta C_\phi(\beta))\}$.
11. Quantify the incompleteness of $P_{m'}$ and determine whether the error has been minimized or not; if not, go to step 2 above for next iteration (by replacing $f_s$ with $f_{s'}$).

Although the subject invention has been described in regard to two dimensional motion, it is applicable to compensating for three dimensional notion, which may be encountered, particularly in industrial CT scanning applications.

While the present invention has been described with respect to certain preferred embodiments thereof, it is to be understood that numerous variations in the details of construction, the arrangement and combination of parts, and the types of materials used may be made without departing from the spirit and scope of the invention.

What I claim is:

1. A method of compensation for motion of an imaged object in computed tomography scanning the motion being associated with expansion and contraction of said imaged object comprising:

determining respective centroids of said object being scanned for each of a predetermined number of successive image scans;

aligning said respective centroids of said successive image scans;

reprojecting an initial image scan to provide an initial projection;

compensating for displacement of said respective centroids between a respective subsequent pilot image scan and said initial projection;

rescaling and realigning the projection data in response to said displacement to improve a reconstructed image; said rescaling being based on the entropy difference between said initial image scan and said pilot image scan; and iteratively continuing said rescaling and said realigning until the effects of motion of said object are reduced to a selected level in said reconstructed image.

2. The method of compensating for motion in computed tomography scanning of claim 1 wherein said scanning and said determining of centroids are parallel beam scanning and said image scans are provided utilizing rectangular coordinates.

3. The method of compensating for motion of claim 1 wherein said realigning includes further aligning of said centroids.

4. The method of compensating for motion of claim 3 wherein said rescaling is based on the relative spread between the reprojections in an interation and said initial projection.

5. The method of compensating for motion of claim 4 including the additional step of retrofitting existing computed tomography equipment to add said method of compensating for patient motion.

6. The method of compensating for motion in computed tomography scanning of claim 1 wherein said scanning is fan beam in scanning and said image scans and determining of centroids are provided utilizing polar coordinates.

7. The method of compensating for motion in computed tomography of claim 6 wherein said fan beam centroid alignment is made insensitive to scan rotation.

8. The method of compensating for motion in computed tomography of claim 7 wherein said centroids of said successive image scans are iterativily aligned an amount related to the amount of misalignment between said successive image scans.

* * * * *